(12) United States Patent
Srivastav et al.

(10) Patent No.: US 8,728,150 B2
(45) Date of Patent: May 20, 2014

(54) MEDICAL DEVICE LOADED WITH FORMULATION FOR TARGETED DELIVERY OF BIOLOGICALLY ACTIVE MATERIAL/S AND METHOD OF MANUFACTURE THEREOF

(75) Inventors: Pradeepkumar Ramkrishna Srivastav, Vapi (IN); Utpal Devendra Thakor, Vapi (IN); Sanjeev Nauttam Bhatt, Mumbai (IN)

(73) Assignee: Meril Life Sciences Private Limited, Vapi (IN)

( * ) Notice: Subject to any disclaimer, the term of this patent is extended or adjusted under 35 U.S.C. 154(b) by 194 days.

(21) Appl. No.: 13/145,386

(22) PCT Filed: Jan. 21, 2010

(86) PCT No.: PCT/IN2010/000036
§ 371 (c)(1),
(2), (4) Date: Jul. 20, 2011

(87) PCT Pub. No.: WO2010/086880
PCT Pub. Date: Aug. 5, 2010

(65) Prior Publication Data
US 2011/0274732 A1    Nov. 10, 2011

(30) Foreign Application Priority Data
Jan. 21, 2009 (IN) .......................... 137/MUM/2009

(51) Int. Cl.
*A61L 31/16* (2006.01)

(52) U.S. Cl.
USPC ......................................... 623/1.42; 424/423

(58) Field of Classification Search
None
See application file for complete search history.

(56) References Cited

U.S. PATENT DOCUMENTS

| | | | |
|---|---|---|---|
| 6,908,622 B2 * | 6/2005 | Barry et al. ................... | 424/423 |
| 2002/0153348 A1 | 10/2002 | Say et al. | |
| 2005/0251245 A1 | 11/2005 | Sieradzki et al. | |
| 2006/0067977 A1 | 3/2006 | Labrecque et al. | |

OTHER PUBLICATIONS

International Search Report dated Sep. 14, 2010 for PCT/IN2010/000036.

* cited by examiner

*Primary Examiner* — Abigail Fisher
*Assistant Examiner* — Daniel L Branson
(74) *Attorney, Agent, or Firm* — Kramer Amado, P.C.

(57) ABSTRACT

The present invention relates to targeted drug delivery of a drug or therapeutic agent through medical devices coated with formulations comprising of therapeutic agent. The coating on medical devices comprises of therapeutic agent(s), affinity vehicle(s) and additives for targeted drug delivery of biologically active material(s). The invention provides a method of manufacturing the formulation, method of coating the medical devices with such formulations to achieve controlled delivery of optimum drug dose at the target site within the body, desirable drug retention on the medical devices in vivo and in vitro and desirable drug release at the target tissue in-vivo. The invention this provides a mechanism to enhance the bioavailability of the therapeutic agent at the target tissue in the treatment of restenosis thereby reduces the actual dose of the therapeutic agent and provides a very thin layer of coating on the surface of the medical device.

14 Claims, 11 Drawing Sheets

MEDICAL DEVICE LOADED WITH FORMULATION FOR TARGETED DELIVERY OF BIOLOGICALLY ACTIVE MATERIAL/S AND METHOD OF MANUFACTURE THEREOF

FIELD OF THE INVENTION

This invention relates to implantable medical devices loaded with formulations comprising of affinity vehicle and additive and therapeutic agent/s and/or drugs and/or genetic materials and/or biological material/s for targeted delivery of therapeutic agent/s and/or drugs and/or genetic materials and/or biological material/s. It also relates to the method of manufacture thereof to achieve desirable drug concentration, and/or drug retention, and/or release in-vivo of therapeutic agent/s and/or drugs and/or genetic materials and/or biological material/s. The invention relates to implantable stents, orthopedic implants, dental implants, etc. with porous and/or plain surface. This invention also relates to non-implantable devices such as balloon catheters loaded with therapeutic formulation in which the therapeutic agent/s and/or drugs and/or genetic materials and/or biological material/s is attached to and/or encapsulated with affinity vehicle/s to facilitate and/or enhance the effective drug delivery into the tissue of a mammalian blood vessel. In the text below, the words "drug", "therapeutic agent" and "biologically active material" are used interchangeably.

BACKGROUND OF THE INVENTION

There are several methods that are known for the delivery of a pharmaceutical composition for the treatment of various medical conditions. The therapeutic agent in a pharmaceutical composition may be delivered to a human or veterinary patient by various routes of administration such as but not limited to subcutaneous, topical, oral, intraperitoneal, intradermal, intravenous, intranasal, rectal, intramuscular, and within the pleural cavity.

One of the methods of administration of a drug is by introducing an implantable medical device containing the desired drug/therapeutic agent in a formulation, partly or completely into/onto the respective site such as but not limited to esophagus, trachea, colon, biliary tract, urinary tract, vascular system or other locations within a human or veterinary patient wherein the medical device may be a stent, catheter, balloon, dental implants, orthopedic implants, etc.

Exposure, however, to a medical device which is implanted or inserted into the body of a patient can cause the body tissue to exhibit adverse physiological reactions. For instance, the insertion or implantation of certain catheters or stents can lead to the formation of emboli or clots in blood vessels. For example, when a medical device is introduced into and manipulated through the vascular system, the blood vessel walls can be disturbed or injured. Clot formation or thrombosis, and/or cell proliferation often results at the injured site, causing stenosis (i.e., closure) of the blood vessel. Additionally, if the medical device is left within the patient for an abnormal period of time, thrombus may form on the device itself with subsequent cell proliferation, again causing restenosis.

Drug-Eluting Stents (DES) are made to resist stenosis or cell proliferation by coating them with therapeutic agents which elute at the target site at a desired rate and desired dose to achieve desired drug concentration in the vessel wall tissue. The rate of release of therapeutic agent in surrounding blood stream and on the surrounding tissue is very important to get desired clinical result, at the same time controlling adverse effects. To control the release rate, the therapeutic agents are coated on stents along with other components like polymers which are biodegradable/bioabsorbable or non-biodegradable/non-bioabsorbable.

Treatment of damaged vascular tissue, thrombosis and restenosis, sees the need for administering therapeutic substances to the treatment site. For example, anticoagulants, antiplatelets and cytostatic/cytotoxic agents are commonly used to prevent thrombosis of the coronary lumen, to inhibit development of restenosis, and to reduce post-angioplasty proliferation of the vascular tissue. In order to provide an efficacious concentration of therapeutic substances to the treated site (site of pathology) by systemic administration of such medication produces adverse or toxic side effects for the patient. Such problem is overcome by way of local delivery wherein smaller levels of medication, as compared to systemic dosages, are delivered to the site of pathology. Local delivery produces fewer side effects and achieves more effective results. Of the techniques applied for local delivery of the drugs, most common is through the use of medicated stents or drug eluting stents.

Recently, various types of drug-coated stents have been used for the localized delivery of biologically active materials to the wall of a body lumen to prevent restenosis. The biologically active materials used as part of the stent coating typically have one or more therapeutic activities such as but not limited to antithrombotic activity, antiproliferative activity, anti-inflammatory activity, vasodilatory activity, or lipid-lowering activity. Generally, biologically active materials are adhered to the stent surface in admixture with a carrier polymer.

A method involving the use of a polymeric carrier along with the therapeutic agent/s coated onto the body of the stent is disclosed in U.S. Pat. No. 5,464,650, U.S. Pat. No. 5,605,696, U.S. Pat. No. 5,865,814, and U.S. Pat. No. 5,700,286. U.S. Pat. No. 5,843,172 and U.S. Pat. No. 6,240,616, report a medicated prosthesis, such as a stent, deployed in a human vessel. The metallic stent in consideration has a plurality of pores in the metal which are loaded with medication. When the stent is implanted into the vasculature of a patient, the medication in the stent dissipates into the tissue of the vasculature close to the stent. The stent may be formed from a porous metal in the form of a wire, tube, or metal sheet. Porous metal is formed by sintering metal particles. In some cases, sintering the particles or fibres is done in several layers.

In another recent prior art, U.S. Pat. No. 5,972,027, expandable intraluminal stents made of a powdered metal or polymer are provided as well as their method of manufacture. These stents are characterized by a desired porosity, with a drug compressed into the pores of the stent. The stents are formed by subjecting one or more powdered materials in a die cavity to a pressure treatment followed by a heat treatment. The material may be cast directly in a stent-like form or cast into sheets or tubes from which the inventive stents are produced. The so-formed porous metal or polymer stent is then loaded with one or more drugs.

U.S. Pat. No. 6,379,381 discloses an implantable stent capable of being loaded with substances. In one example, the prosthesis is a cylindrical-shaped body having depots or pores formed thereon. The depots can be formed at pre-selected locations on the body of the stent and can have a pre-selected depth, size, and shape. The depots can have various shapes including a cylindrical or a conical shape. Such depots are formed as laser trench. Laser fabrication and physical/chemical etching techniques well known to one of ordinary skill in the art have been used. Substances such as therapeutic substances, polymeric materials, polymeric materials containing therapeutic substances, radioactive isotopes, and radio-opaque materials can be deposited into the depots.

The US patent application no. 2006/0085062 discloses an endolumenal stent system for promoting endothelialization of vascular injury sites, comprising: an endolumenal stent; a porous surface on the endolumenal stent having a plurality of pores; and a composite material located within each of the pores and comprising a bioerodable polymer in combination with a therapeutically effective amount of a bioactive agent.

While the polymer provides the drug-coated stent with several important functions, the use of the polymer also burdens the stent with certain disadvantages. Often, coating the biologically active material with a polymer can result in drug entrapment within the polymer coating so that the biologically active material diffuses from the stent to the area to be treated too slowly and/or at too low a concentration. Moreover, conventional coating methods typically use a continuous phase coating such as a liquid carrier polymer phase to dispose the biologically active material on the stent. Such methods often result in disposing an excess amount of polymer on the stent surface. The presence of excess polymer is generally considered to be detrimental to tissue recovery, and a bare metal stent is believed to promote better vascular healing than a stent having a polymer finish.

Further, these polymers cause inflammation to the arterial wall leading to in-stent restenosis (ISR). Other distinct factors that cause ISR include neointimal hyperplasia and other well known cardiovascular complexities. Substantial research is being carried out to eliminate the negative/adverse effects of vascular stenting by eliminating the use of polymeric material for therapeutic coating of the stents.

Obstacles often encountered with the use of a polymeric coating include difficulties in coating a complicated geometrical structure, poor adhesion of the polymeric coating to the surface of a stent, and biocompatibility of the polymer.

US patent application no. 2003/0064965 discloses a medical device which comprises: a plurality of particles, which are supported within the matrix of a macrostructure, dispersed on the surface of the medical device, each particle comprising a therapeutic drug or a combination of therapeutic drugs having anti-proliferative activity in the cardiovascular system, wherein the particles are selected from the group consisting of liposomes, microparticles, nanoparticles, and drug aggregates, and wherein the medical device is contacted with a tissue or circulation such that the drug is released from the particle into the surrounding tissue or blood circulation in less than 5 minutes after the contacting step. The macrostructure is selected from the group consisting of fibrin gels, hydrogels and glucose and the particles are supported within the matrix of a macrostructure. This formulation is specifically suitable for medical devices like balloon catheters which remain in the body for short time. This formulation can not be used where sustained release is required over a long period of time varying from a few days to 60 days.

US patent application No. 2008255509A1 describes a coated medical device for rapid delivery of a therapeutic agent to a tissue in seconds or minutes. The coating contains a therapeutic agent, at least one of an oil, a fatty acid, and a lipid, and an additive. The additive has a hydrophilic part and a drug affinity part which is one of the hydrophobic part which has affinity to therapeutic agent by hydrogen bonding or van der Waals interactions. This formulation is specifically suitable for medical devices like balloon catheters which remain in the body for a short time during which the drug should be delivered to the target site like a tissue. This formulation can not be used where sustained release of therapeutic agent is required over a long period of time.

Disadvantages associated with the aforementioned methods are (1) quite a lot of the drug is lost in the blood; (2) only a fraction of the drug is able to reach the target cell/tissue, which necessitates incorporation of high drug dose on the medical devices e.g. stent to achieve efficacious drug dose in the target tissue; (3) very fast release of therapeutic agent; (4) a narrow range of release kinetics and (5) a part of the drug and delivery vehicle residing for a long time or permanently on the stent surface after implantation causes inflammation, delayed healing and incomplete endothelialization which in turn results into acute, sub-acute and late thrombosis. In some cases, the entire quantity of drug and/or the vehicle is not released.

Non polymeric compositions for coating a medical device are described in patents/patent applications. Patent applications US20080206305A1, US20080109017A1 and US20080113001A1 describe a barrier device having one or more barrier components in plurality of tiers that exhibit modulated healing properties, anti-inflammatory properties, non-inflammatory properties, therapeutic properties, and/or adhesion-limiting properties. The barrier component can be a non-polymeric cross-linked gel (comprising molecules covalently cross-linked into a three-dimensional network) derived at least in part from a fatty acid compound or a biocompatible oil (naturally occurring oil, such as fish oil, cod liver oil, cranberry oil, or other oils having desired characteristics which may be partially hydrogenated to get a wax to allow the oil to adhere to a device for a longer period of time) and may include a therapeutic agent. The barrier component, though non-polymeric, is a cross-linked gel.

Application No. WO2007011385A2 describes a method of curing to form a gel, comprising a non-polymeric substance and determining an amount of cross-linking desired within the substance as a result of curing by applying heat at a selected temperature for a selected time period to achieve desired amount of cross-linking to form the gel.

Patent application US20060083768A1 describes method of increasing the viscosity of an oil-based composition comprising at least one fatty acid (and salts); and combining the oil-based composition with one or more therapeutic agents in an amount sufficient to increase viscosity of the oil based composition. The method comprises (optionally) the step of mixing the therapeutic agents with a solvent prior to combining the therapeutic agent with the oil-based composition. The viscosity increases from about 5 cPs to about 150,000 cPs. The release of the therapeutic agents is extended by the increased viscosity of the oil-based composition which prevents the removal of the coating from a medical device in vivo.

Patent application No. US 2005/0251245 describes methods of forming pores on a surface. The porous portion is attached to or integrated into the main structure of the medical device such as stent. The method of forming pores is mainly chemical where a voltage application to aid the chemical etching is mentioned. The etching method is described in general for metals specifically for stainless steel. The surface is prepared for doping the elution material on the porous surface. However, it does not reveal parameters for forming desired pore structure. Method of doping the surface is not revealed.

Patent application Nos. US20080181928A1 and WO2008077248A1 describe depositing a porous layer of ceramics and other materials on medical device by electrochemical deposition, electrophoretic deposition (EPD), sol gel processes, aero-sol gel processes, biomimetic (BM) processes, spraying, and dipping. A coating is applied on this surface where coating comprises a dry film comprising lipid bilayer and pharmaceutically effective agent/s wherein the coating is free of a polymer. The lipid bilayer comprises lipid/s capable of forming a liposome encapsulating the pharmaceutically effective agent when exposed to an aqueous solution.

SUMMARY OF THE INVENTION

The present invention relates to an implantable medical device coated with a formulation comprising of highly biocompatible vehicles devoid of any polymer and which is capable of—(a) delivering the therapeutic agent at the target site with very high or nearly complete drug availability to the target cell/tissue (b) optimum retention of the drug on the stent during its passage till it reaches the target site and (c) capable of inhibiting smooth muscle cell proliferation and also effect desired endothelialization.

In accordance with one of the aspects of the present invention it provides a formulation capable of being coated onto the surface of the medical device that may be porous and/or plain.

In accordance with one of the aspects of the present invention it provides a formulation, which is cable of covering the entire surface of a medical device uniformly and that adheres to the surface of the medical device with enough force to withstand forces applied to the device during its manufacture (e.g. during crimping operation of a stent on the balloon of a catheter) and its implantation to the target site without damaging the coating or loss of any component of the coating including the therapeutic agent/s.

A still further object of the present invention is to provide a formulation capable of delivering biologically active materials including therapeutic agent/s, drugs, genetic materials and biological materials. Therapeutic agents include heparin, heparin derivatives or its analogs, urokinase, hirudin, tacrolimus, everolimus, rapamycin (sirolimus) or its analogs or derivatives, paclitaxel or its analogs or derivatives, aspirin, antiproliferative agents, antioxidants, antibiotic agents, vitamins, steroids, and other therapeutic agent/s capable of altering the cellular metabolism or inhibiting a cell activity (such as protein synthesis, DNA synthesis, spindle fiber formation, cellular proliferation, cell migration, microtubule formation, microfilament formation, extracellular matrix synthesis, extracellular matrix secretion, or increase in cell volume). The genetic material includes DNA or RNA (including, without limitation, of DNA/RNA encoding a useful protein, intended to be inserted into a human body including viral vectors and non-viral vectors). The biological material includes cells, yeasts, bacteria, proteins, peptides, cytokines and hormones, peptides and proteins (including various growth factors, inducible factors, derived factors, cell factors, cell growth supplements, colony stimulating factors, growth differentiation factors, modulating factors, growth hormones thymidine kinase inhibitors, platelet receptor antagonists, anti-thrombin antibodies, anti-platelet receptor antibodies, platelet inhibitors, vascular endothelial growth factors, growth factor receptors, growth factor inhibitors, growth factor receptor antagonists, inhibitory antibodies, antibodies directed against growth factors, agents which interfere with endogenous vasoactive mechanisms, smooth muscle cell inhibitor etc.

In accordance with one aspect of the present invention an implantable medical device is provided having an ultra thin coating of the formulation having anti-inflammatory properties.

In yet another embodiment of the present invention, it provides a formulation, which gets discharged completely from the surface of the implantable medical device in the vicinity of the target site over desired time period.

In yet another embodiment of the present invention an implantable medical device having porous surface is provided.

As per one of the embodiment of the present invention it provides an implantable medical device such as stent coated with a formulation having therapeutic agent, affinity vehicle and additive but non-polymeric in nature thereby reducing or eliminating artery wall inflammation.

It is one of the aspect of the invention to provide a range of release kinetics (varying from several hours to several days) of the therapeutic agent from the surface of the device in the vicinity of the target site by varying concentration of the ingredients of the formulation and physical properties of the surface of the device.

Yet another aspect of the present invention is to provide an easy and simple method for pore formation of the surface of the device and loading methods thereof.

Yet another aspect of the present invention is to provide a suitable porous surface for the medical device, which facilitates growth of tissue by cell anchoring without promoting adverse activation of platelets and leucocytes, thus promoting early endothelialization.

Yet another embodiment of the present invention is to enhance the bioavailability of the therapeutic agent in the target vessel wall tissue with minimum drug loss during the transit and at a comparatively much lower drug dose on the surface of the implantable medical devices compared to those currently in vogue and still achieve comparable or higher drug absorption by the target tissue.

Accordingly, in one aspect, the present invention provides an implantable medical device coated with a drug formulation capable of delivering drug at the target site with optimum and nearly complete drug availability to the target tissue and thereby providing an optimum retention of the drug on the stent during the passage till target tissue.

Further, the invention provides an implantable endoluminal body having a surface which is devoid of pores with at least one therapeutic agent and at least one affinity vehicle with an additive loaded onto the surface of said device for being released at the target site over a desired period of time that has the effect of enhancement in the bioavailability of the therapeutic agent.

In another aspect, the invention provides pre-loading methods, which includes loading of the implantable medical device with the formulation comprising of one or more therapeutic agents with other substances like affinity vehicles and additives (henceforth termed as formulation). The formulation either adheres to the plain surface of the device or enters into and adsorbs onto the pores (if the surface of the device is porous) fully or partially depending on pore structure, molecular size of the components of the formulation and the formulation loading process.

In yet another aspect, the present invention provides a formulation which essentially comprises of at least one therapeutic agent with at least one affinity vehicle and an additive suitable for considerably lower drug dose onto the surface of the implantable device compared to those currently in vogue and still achieve comparable or higher drug concentration on the target tissue.

In a further aspect, the invention provides a preparation method of inventive formulations useful for loading on to the surface of the implantable medical devices such as stents, orthopedic & dental implants etc.

According to aspects of the present invention the medical device can include any of a stent, a catheter and a balloon.

As per the aspects of the present invention the phrase controlled release generally refers to the release of a biologically active agent in a predictable manner over the time period of days, weeks or months, as desired and predetermined upon the coating of the formulation comprising of therapeutic agent on the surface of the medical device from which it is being released. An added advantage of the oil/lipid/fatty acid based formulations is that they give coatings which are lubricious. Such lubricious coating minimizes injury and inflammation resulting into early endothelialisation.

The present invention has been described with particular reference to stents. However, the present invention can be applied to all implantable devices, such as orthopedic & dental implants etc and non-implantable devices like balloon catheters etc. The present invention is applicable to temporary as well as permanent implants.

DETAILED DESCRIPTION OF THE INVENTION

For the purpose of this invention, the expression "endoluminal body"; "implantable medical device" and "stent" are used interchangeably.

The stent is made from biocompatible materials like metals such as stainless steel, Cobalt-chromium alloys, Nickel-Titanium alloys (Nitinol), Titanium, Platinum, Magnesium etc. and polymers by standard and well known stent forming methods. The metallic stent surface can be treated to make it suitable for pore formation process.

According to the present invention, the surface of the implantable metallic medical device is treated to make it porous in nature. A porous surface would mean a surface containing cavities which are nanometers to micrometers in dimensions. These cavities are also referred to as "pores". The porous surface is so tailored as to hold specific quantity of desired formulation of affinity vehicle/s and/or other therapeutic agents including drug/s and/or additives and/or also to facilitate growth of tissue by cell anchoring without promoting adverse activation of platelets and leucocytes, thus promoting early endothelialization.

The said cavities or pores on the surface carry a therapeutic dosage of an agent or in the alternative; the therapeutic agent is encapsulated in or attached to or mixed with a carrier vehicle (affinity vehicle).

The therapeutic agent of choice or combinations of therapeutic agents may be formulated and/or encapsulated using sonication techniques so as to increase it's/their bioavailability to produce the desired effect and for site specific delivery when loaded onto the stent surface (which may or may not be porous) in such a way so that almost all of the loaded biologically active material/s from the device reaches the target tissue and remains there in required amounts for required time.

The methods for preparing the formulations include use of lipids (as such or hydrogenated) and/or liposomes as affinity vehicles for site specific delivery of therapeutic agent/s, particularly for preventing artery inflammation and restenosis. The affinity vehicle stores the therapeutic agent as well as allows the therapeutic agent to diffuse uniformly and in a controlled manner into the lumen of the tissue in which the medical device has been implanted. The affinity vehicle is designed to effect controlled delivery of the therapeutic agent in the target tissue minimizing the loss of drug into the blood stream.

Figure 1:
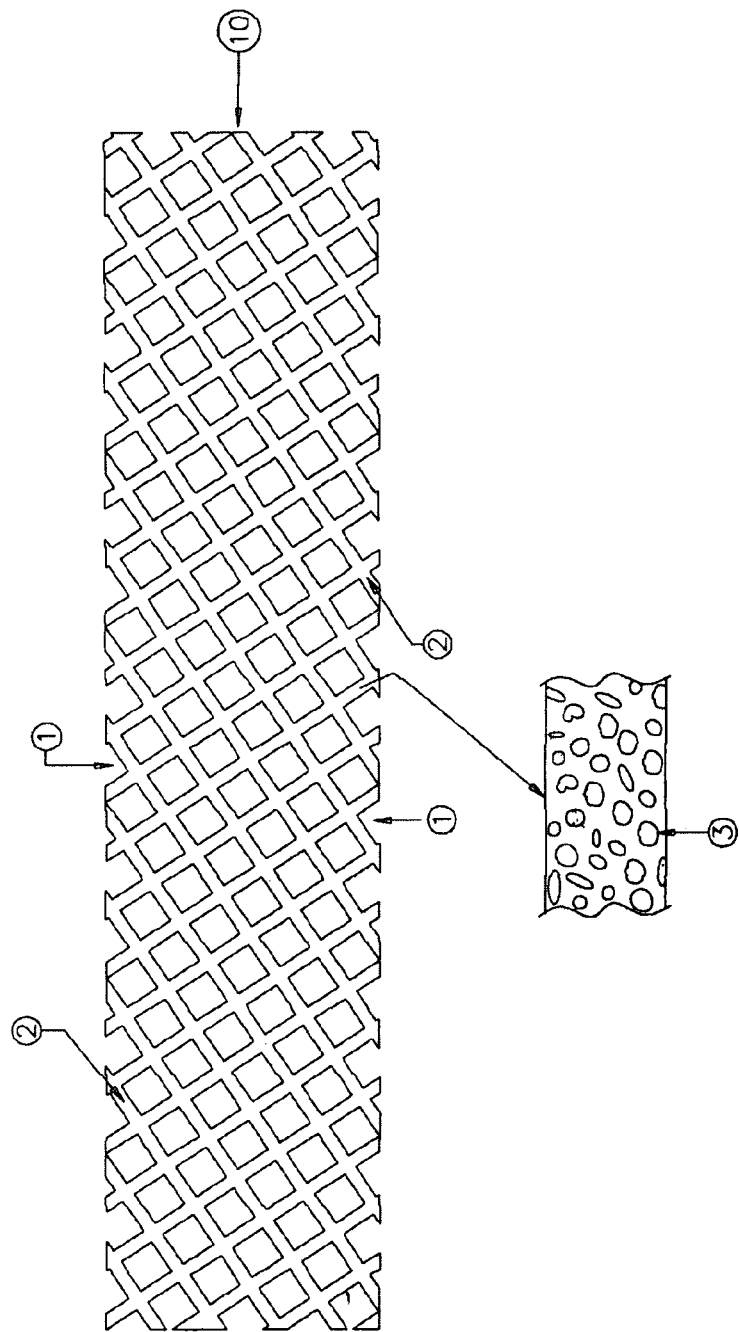
FIG. 1 depicts an endoluminal body having porous surface.

The preferred embodiment of the present invention can be illustrated with reference to FIG. 1. FIG. 1 depicts an implantable medical device (10) which comprises of an endoluminal body with a surface (2) which may be plain or having plurality of randomly or unrandomly distributed pores/cavities (3). The therapeutic agent loaded onto this device is either adhered to the plain surface of the device or adsorbed into the said cavities in such a way that the formulation enters into the pores and/or coated onto the surface of the body of the medical device. The said formulation may be formulated using the affinity vehicle, solvent and the additive and then applied in an appropriate manner onto the surface of the device.

Figure 2:
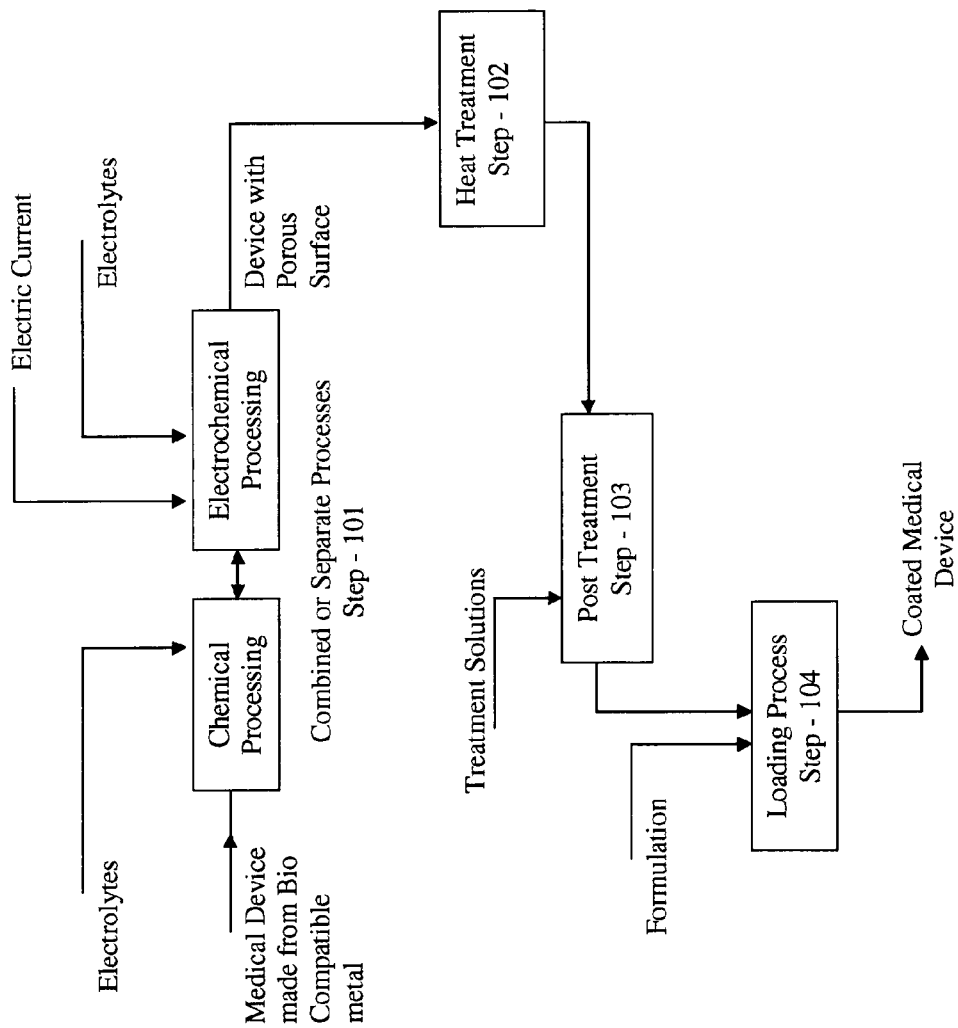
FIG. 2 depicts schematic representation of pore formation process of implantable medical device.
Figure 3:
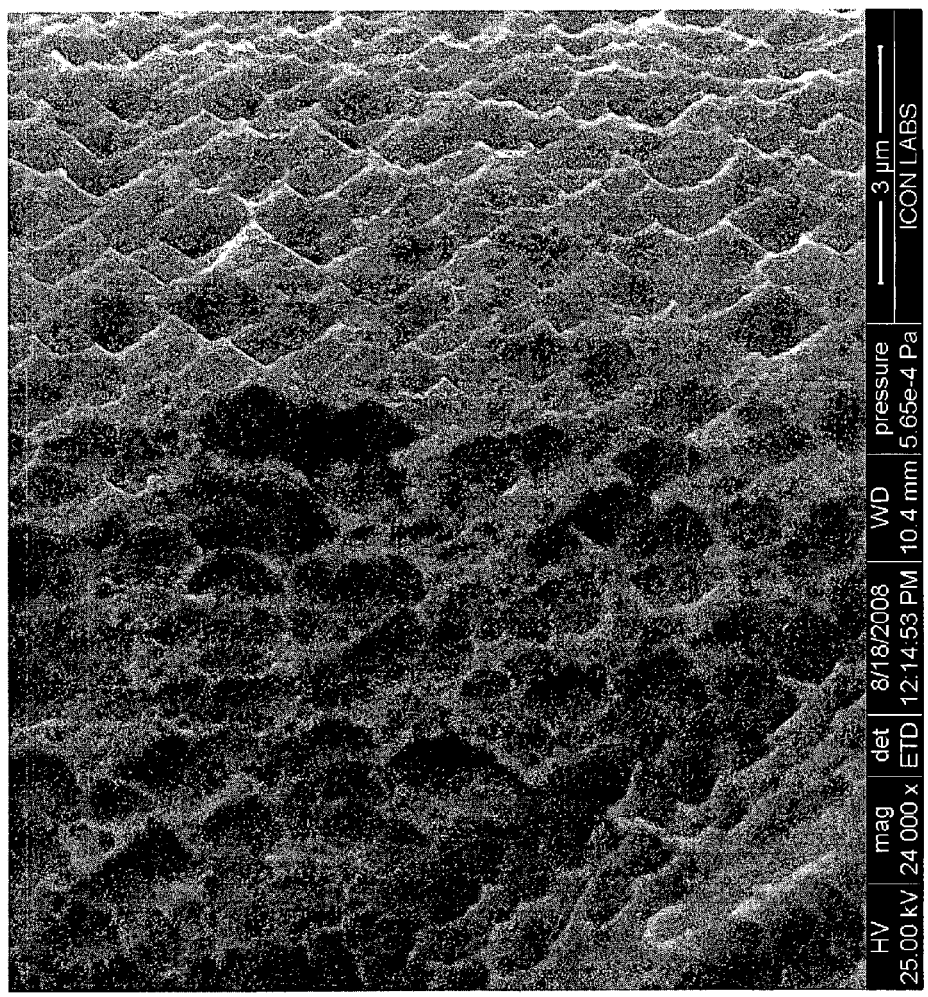
FIGS. 3 to 7 depict the Scanning Electron Microscope (SEM) images of various pore structures obtained on metallic stents.
Figure 4:
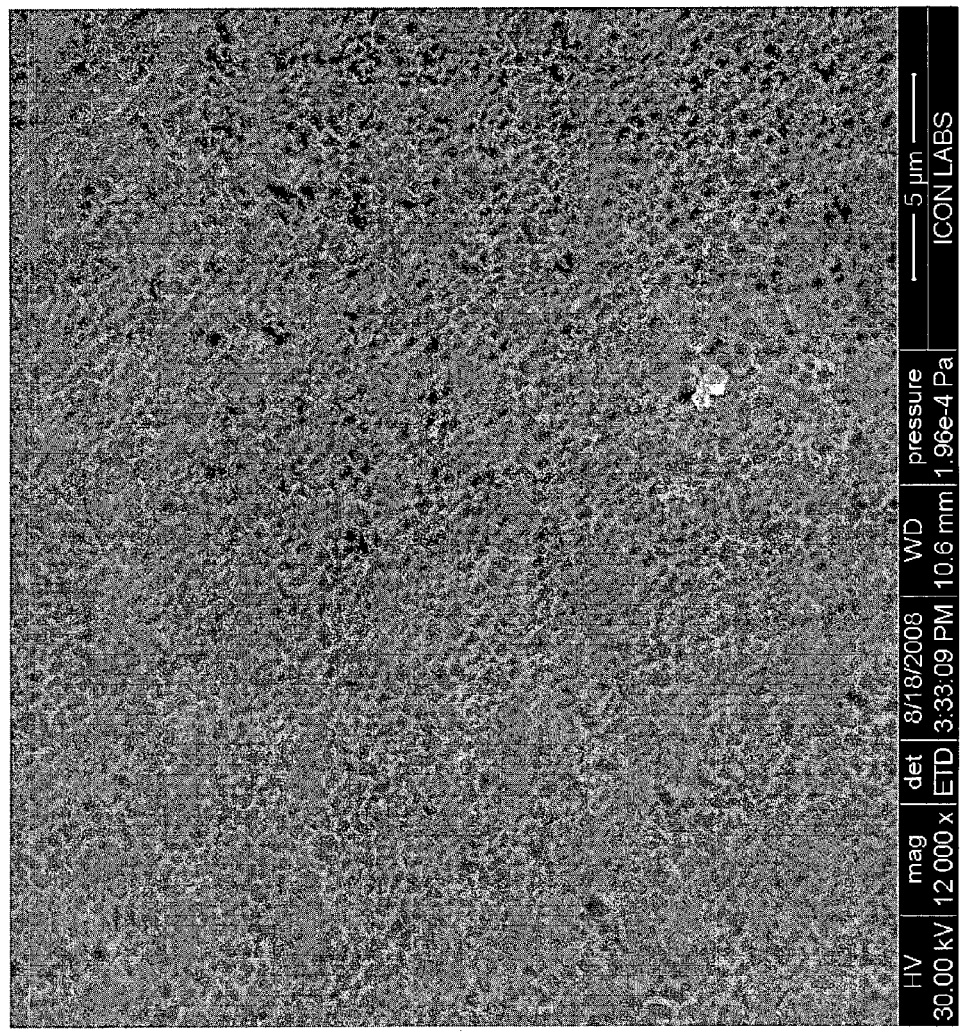
Figure 5:
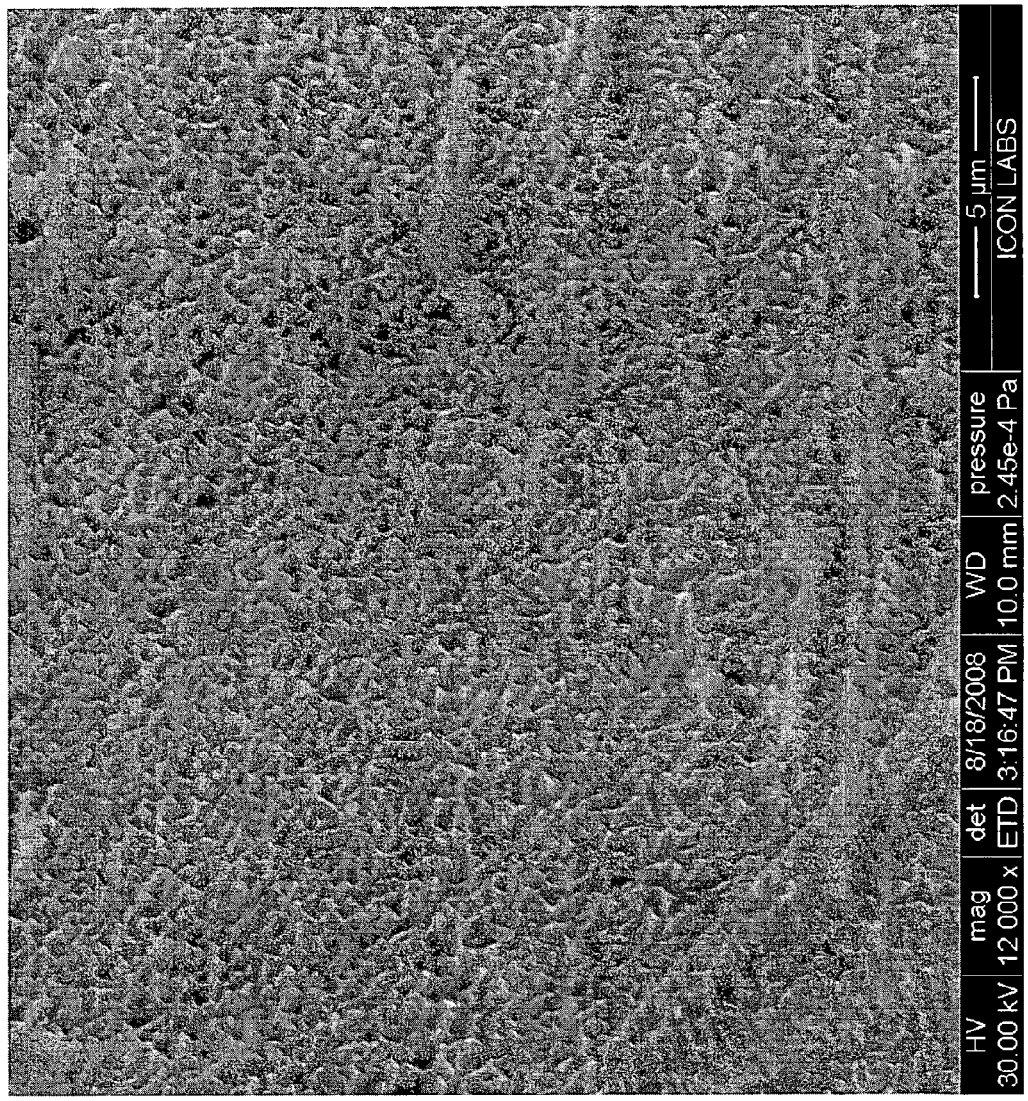
Figure 6:
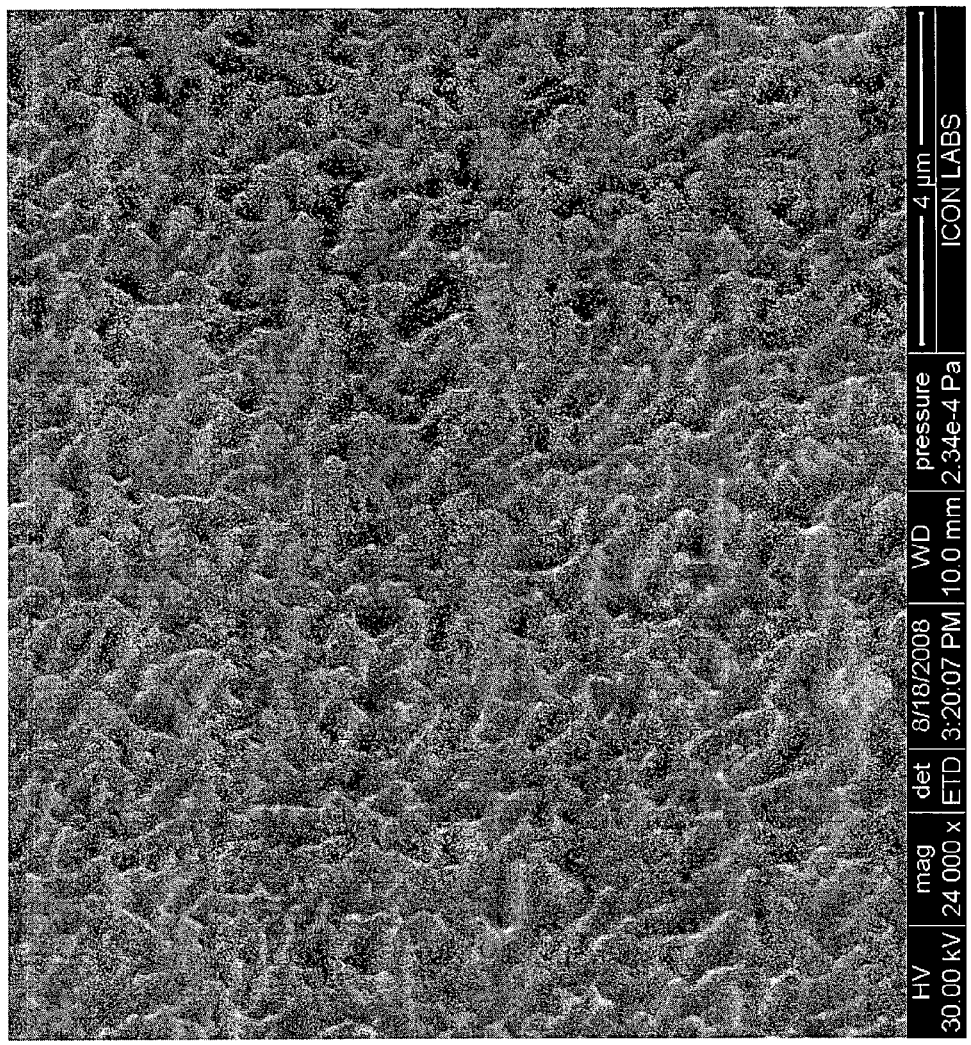
Figure 7:
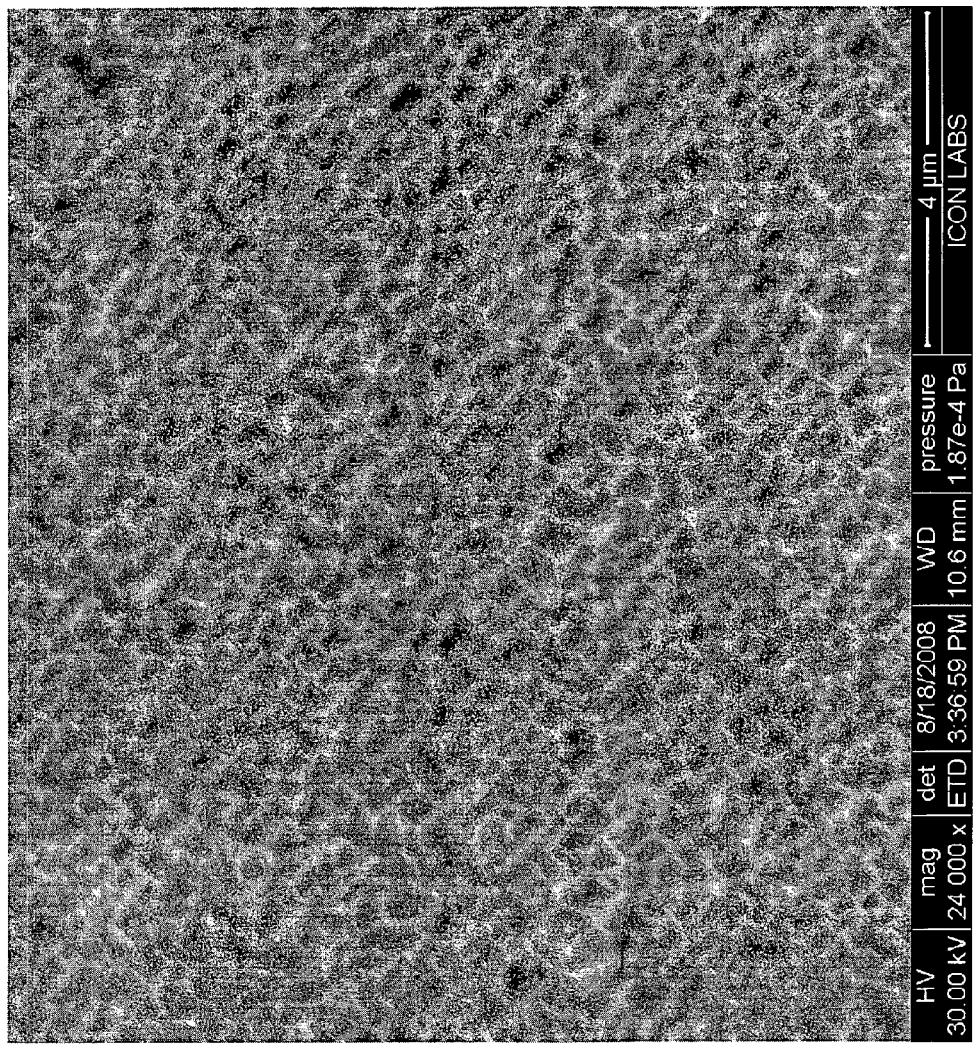
Figure 8:
FIGS. 8 and 9 depict the Scanning Electron Microscope images of struts of stent (without pores) coated with the formulation after crimping on the balloon of a catheter.
Figure 9:
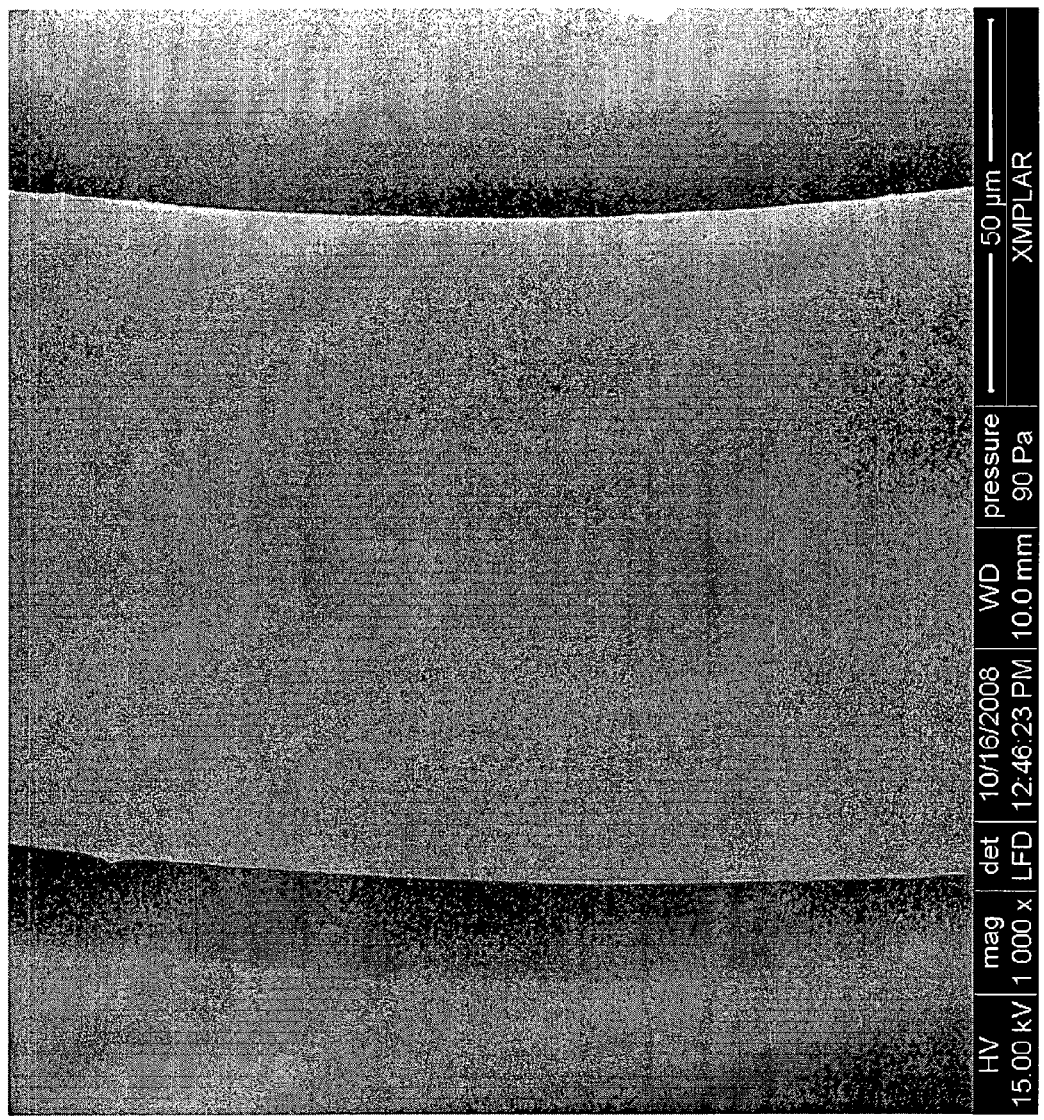
Figure 10:
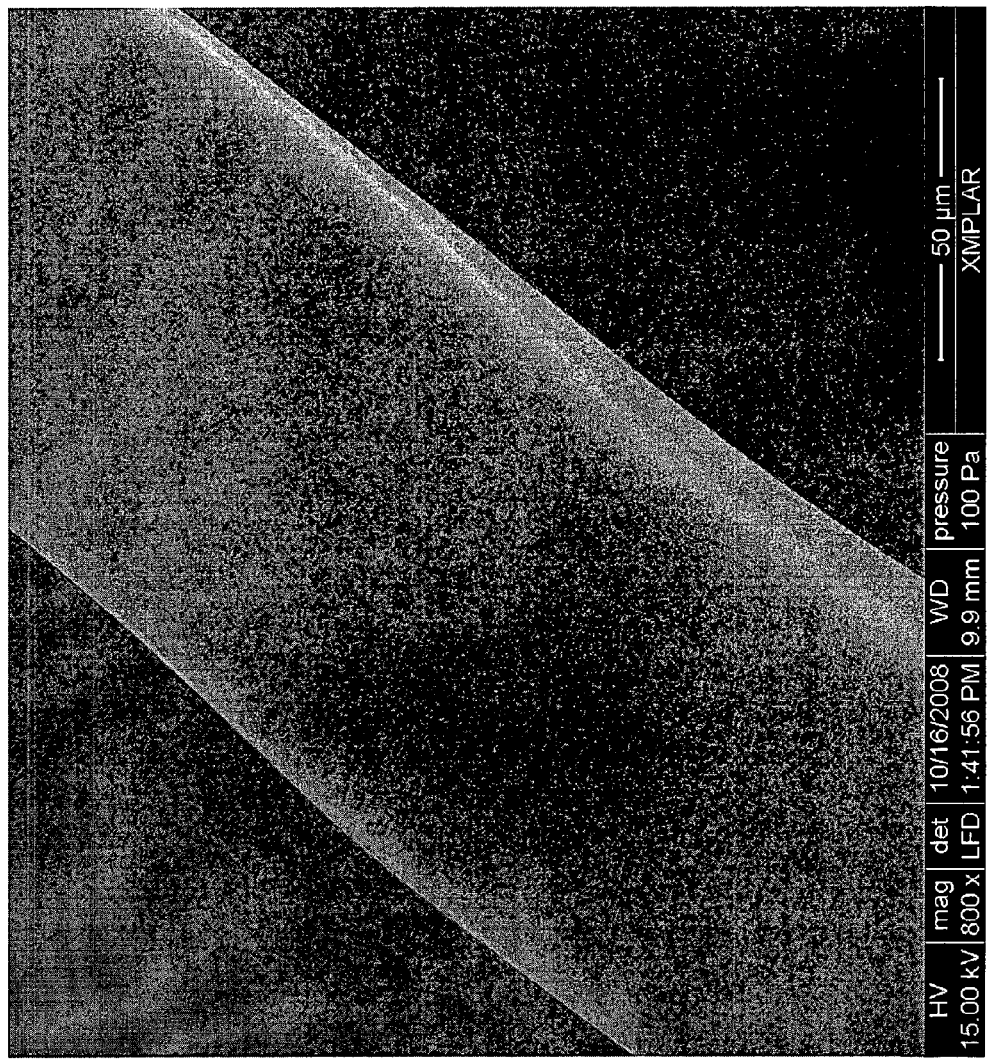
FIGS. 10 and 11 depict the Scanning Electron Microscope images of struts of same stent after expansion of the balloon of the catheter. As is evident, the coating remains intact on crimping and after expansion.
Figure 11:
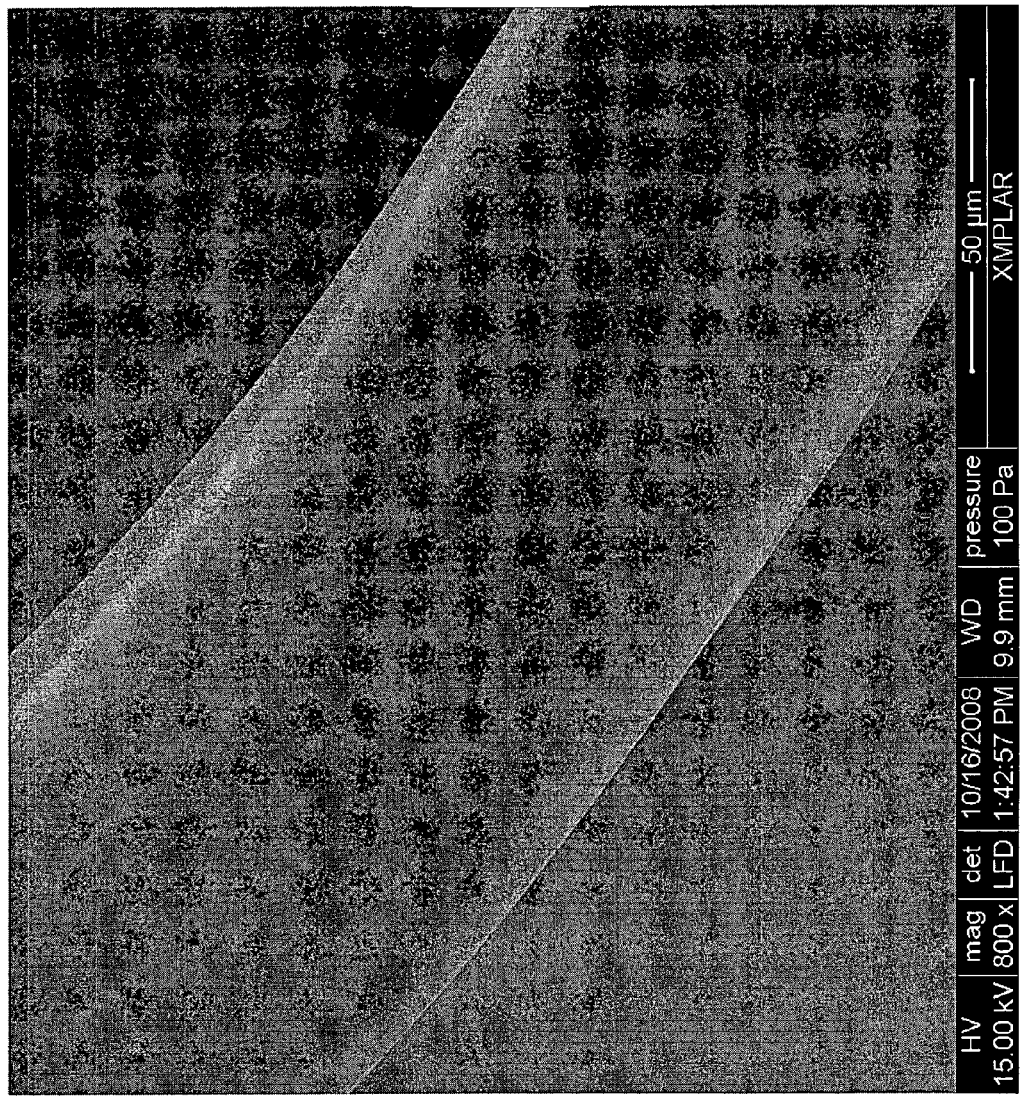

In another preferred embodiment, various porous surfaces are illustrated with the help of FIGS. 3 to 7 which show the Scanning Electron Microscope (SEM) images obtained on metallic stents through the process shown schematically as in FIG. 2.

In another preferred embodiment, coating of the formulation is illustrated with the help of FIGS. 8 to 11 which show Scanning Electron Microscope images obtained on metallic stents before and after expansion.

In another aspect of the present invention, surface modification of implantable medical device is disclosed. The surface modification process includes pore formation and loading of the therapeutic formulation over the said pores and/or on the plain surface of the device. The method for manufacturing porous implantable medical devices includes the pore formation process.

Accordingly, a method of manufacturing an implantable medical device with porous surface for providing local delivery of therapeutic agent at an implantation site comprises of:

a) treating the surface of the implantable medical device with specific chemicals and/or b) treating the surface of the implantable medical device with electrochemical process to make it porous by providing a plurality of porous holding cavities open to one side;

c) optionally, subjecting the said device with pores to post heat treatment methods;

d) meanwhile, preparing the formulation comprising of at least one therapeutic agent with at least one affinity vehicle such as lipid or modified lipid or combination thereof, solvent and an additive, which may be optionally sonicated prior to or during coating process to effect encapsulation or formulation of the therapeutic agent/s into the affinity vehicle to considerably enhance the delivery of the encapsulated/formulated therapeutic agent/s into the injured/diseased tissue using the medical device eventually resulting into majority of the therapeutic agent/s getting delivered to the injured/diseased tissue using the medical device; and e) loading the therapeutic agent(s) and affinity vehicle(s) together with additive and solvent onto the plain surface of the device (with no pores) or onto the surface of the device with cavities formed on the surface.

The manufacturing process as mentioned supra and as described schematically in FIG. 2, comprising the pore formation process which includes step 101 of treating the bare metal stent with specific chemicals including but not limited to mineral acids (like but not limited to Hydrochloric acid, Sulfuric acid, Nitric acid, Phosphoric acids, Chlorosulfonic acid, Oleum etc), organic acids; including alicyclic and hetero cyclic acids (like but not limited to Acetic acid, mono-, di- or tri-halogenated acetic acid, halogenated or non-halogenated acetyl chlorides, substituted or un-substitited benzoic acid, picric acid, fatty acids, amino acids, ascorbic acid, hydrochlorides of organic amines, substituted or unsubstituted phenols, etc), alkalis (like but not limited to caustic soda, caustic potash, lithium hydroxide etc), salt solutions (like halides of metals like Sodium, Potassium, Iron, Aluminum etc. viz. sodium chloride, potassium chloride, ferric chloride, aluminum chloride etc), oxidizing agents (like alkali metal chlorates, chromates, dichromates, permanganates, air, oxygen, ozone etc), reducing agents (like hydrogen, alkaline formaldehyde, aldehydes etc) etc. either individually or in combination, with a specific sequence. The treatment may be carried out under inert or normal or oxidizing atmosphere and under programmed and strictly controlled time-temperature profiles for each individual step. The oxidation processes may be carried out in presence of catalysts like salts of Selenium, Cobalt, Manganese etc or other catalysts known in chemical science. Similarly, reduction processes with hydrogen may be carried out in presence of catalysts like Raney Nickel, supported metals like Nickel, Platinum etc and their salts or other catalysts known in chemical science. The processes may be carried out individually or in combination. For example, treatment with acids may be carried out with passage of oxygen or air through the solution with or without catalyst. The processing is once through or repetitive over several cycles with the same or different time-temperature profiles.

The method may or may not include electrochemical step in combination with chemical contacting or separately using electrolytic solutions. The electrolytes are selected from a variety of inorganic and organic salts and salt mixtures with ionic bonds having compatible ions. The choice also depends on the relative positions of these ions in the electrochemical series. The electrolytes are maintained at specific pH (ranging from highly acidic to highly alkaline, preferably acidic) to achieve desired etching. The electrochemical step may be a single step or repeated several times in series or alternating with chemical contacting steps. The current passed in electrochemical step may be constant, variable, intermittent or in step wise manner to achieve desired results (current may vary from 70 mA to 100 mA). The time for applying electric current has also pronounced effect on the pore structure and can be used as a control parameter (time may vary from 5 minutes to 20 minutes). Composition of the electrolyte (in the range of 15% to 30% w/w in aqueous solution), temperature of electrolytic bath (in the range of 40° C. to 60° C.), the process environment and processing time (5 minutes to 20 minutes) in electrochemical step/s are manipulated to get desired results.

The concentration of chemicals during the treatment varies from 1% to 30%, preferably between 3% and 20%. The processing temperature varies from 20° C. to 100° C., preferably between 40° C. and 80° C. The processing time for single step process varies from ½ hour to 4 hours. Total time in case of multistep process does not exceed 6 hours.

Chemical etching process may be combined with electrolytic process to achieve desired pore structure on the medical device. Electrolyte solution for the electrolytic process is made with desired components with desired concentration. In a specific embodiment it may be 5-10% hydrochloric acid solution. This solution may contain specific amount of corrosion inhibitor (like but not limited to amines, phosphates, phosphonates, chromates etc) to get proper etching effect without high corrosion. The corrosion inhibitor is chosen to synergize with the electrolyte components.

Desired quantity of this electrolyte solution is added to the electrolytic bath. In a specific embodiment, this quantity is 800 ml to 1500 ml. The temperature of the electrolytic bath is brought to desired value and maintained at this value within ±2-5° C. using temperature control methods. In a specific embodiment, the temperature is maintained at 50±3° C. A cathode ring is introduced into the bath and connected to negative terminal of a DC power supply. Stent is introduced in the electrolytic bath and connected to positive terminal of a DC power supply. Desired current is passed through the system for specific period of time. The magnitude of current and duration of current passing depends on size of the stent and degree of etching required. In specific embodiment, for stents made of Cobalt Chromium alloy, current varied from 50-110 mA and time from 3-10 min for stent diameter of 3 mm and length varying from 8 mm to 40 mm to achieve a surface with specific etching effect. The process may be done in a single step or multiple steps with varying conditions. After each step the stent is cleaned. In a specific embodiment, the process is carried out in two steps. After first step, the stent is cleaned with water at 60-70° C.

After electrolytic etching, the stent is cleaned. Depending on pore structure requirement, the stent may also be subjected to one or more heat treatments at specific temperature (varying between 50° C. and 200° C.) and specific time duration (varying from 2 hours to 12 hours for single step process and maximum 12 hours for multistep process at desired temperature) as in Step 102. In a preferred embodiment, the stent may be subjected to heat treatment where it is maintained at a specific temperature (up to 120° C.) for time up to 3 hours preferentially at 80±5° C. for 2 hours.

All these processes yield desired pore structure. The porous surface may have a uniform or random pore structure or an oriented or directional grain porous structure or a mixture of these types.

Step 103 comprises of suitable post treatments like cleaning, passivation, heating, aging and physical treatment in media like, but not limited to, de-ionized water, organic solvents with promotional additives etc.

The processing etches the stent surface in preferential manner with no or partial oxidation of metal atoms on the surface. This processing creates cavities on the surface that are 1 nanometer to 1.5 micrometers in size and 10 nanometer to 3 micrometers in depth. The porosity of the stent surface may vary from 1% to 99% of the total stent surface. The size distribution of pores and surface coverage can be controlled by manipulating the process conditions. The pore size distribution is made suitable to the formulation of the therapeutic agents and desired loading philosophy to achieve desired release kinetics. The pore structure and formulation composition can be designed to achieve nearly 100% availability of therapeutic agent/s and other components in the coating, leaving only metallic medical device in the artery.

The processing etches the stent surface in preferential manner with no or partial oxidation of metal atoms on the surface. This processing creates cavities on the surface that are within a particular size and depth. The porosity of the medical devices surface may vary in a particular range of the surface of the medical device. The size distribution of pores and surface coverage can be controlled by manipulating the process conditions. The pore size distribution is made suitable to the formulation of the therapeutic agents and desired loading philosophy to achieve desired release kinetics. The pore structure and formulation composition can be designed to achieve nearly 100% availability of therapeutic agent/s.

The pore formation is controlled in such a way that the mechanical properties of the medical device are not changed. The properties of the medical devices, say stents, like radial strength, pushability, trackability, elastic recoil etc. remain essentially unaltered. The pore forming process is controlled so that it does not affect the corrosion properties of the device material adversely.

The porous surface can be designed to facilitate growth of tissue by cell anchoring without promoting adverse activation of platelets and leucocytes, thus promoting early endothelialization.

In step 104, the implantable medical device is loaded with the formulation comprising of one or more therapeutic agents with other substances like affinity vehicles, solvent and additives (henceforth termed as formulation). The formulation can be coated onto the medical device having a plain surface (no pores) or porous surface. When coated on the porous surface, the coating adheres partly to the plain surface of the device and partly enters into and adsorbs onto the pore structure fully or partially depending on pore structure, molecular size of the components of the formulation and the formulation loading process. The composition of the formulation and the surface characteristics (plain or porous) play an important role in releasing the formulation. In case of porous surface, pore structure and the mode of adsorption of the formulation are important in releasing the formulation adsorbed onto the pores. The formulation is adhered to the plain surface or held in the pores by a variety of forces like capillary and Van-der-Waals forces. The physical release of such adhered and/or adsorbed formulation will follow a rate kinetics depending on affinity that the formulation has towards the surface on which it is adhered and/or adsorbed and the driving force exerted by the surrounding environment (like blood stream, tissue, biodegradation/bioabsorption of the biodegradable/bioabsorbable components etc.) which tries to pull the formulation out from the surface of the medical device which may be plain or porous. The release rate of the formulation depends on the difference between the driving force exerted by the surrounding environment and the affinity of the formulation towards the surface and pores and pore structure. Larger the difference, faster is the release of the formulation. A threshold value of this difference is required to start the release process. In extreme cases on either side, the formulation may not get released at all or may release instantaneously. The affinity of the formulation and the driving force can both be further manipulated by presence of other materials like affinity vehicles. The release kinetics can thus be tailored to suit the clinical requirements by keeping the surface of the medical device plain or making it porous (with full or partial porousity and modifying the pore structure) and the composition of the formulation. The release kinetics strongly depends on the affinity of the formulation to adhere to the plain surface and/or adsorb onto the porous surface.

The hydrophilicity and hydrophobicity of the formulation play very important role in the release kinetics and target delivery of therapeutic agent/s into the tissue and the loss of therapeutic agent/s into the blood stream. The formulation can be tailored to adjust these properties favorably such that the device delivers maximum therapeutic agent/s in to the tissue with very little loss to the blood stream. This tailoring of the formulation can be used advantageously to achieve desired clinical performance even at doses of therapeutic agent/s which are much lower than those currently in vogue. This will reduce the quantity of the coating which will result in to a coating which is comparatively thinner.

The formulations and the coating methods can be designed to make them effective and suitable for the plain non-porous stent surface without compromising on the positive adhesion aspects of the stents with pores.

The method of coating of the formulation and the properties of the formulation can be optimized to provide uniform thin coating over the entire surface of the medical device. The adhesion of the formulation to the stent surface (which may or may not be porous) is strong enough to withstand forces applied during crimping of the stent on the catheter and handling during its deployment in the artery. The release kinetics of the formulation can be adjusted such as to effect release in desired time period ranging from hours to days.

The desired therapeutic agents may be chosen from a host of products known to have the right effect on prevention of restenosis. These therapeutic agents may include anti-proliferative agents, anti-inflammatory agents and anti-thrombotic agents. The drugs may include paclitaxel and its analogs, drugs of the monocyclic lactone family (for example, Sirolimus, Everolimus, Zotarolimus, their other analogs and derivatives etc) and other such drugs.

The term "biologically active material" as used in the present invention encompasses therapeutic agent, drugs, genetic material, and biological material and can be used interchangeably with "therapeutic agent" and "drug". Non-limiting examples of suitable therapeutic agent include heparin, heparin derivatives, urokinase, dextrophenylalanine proline arginine chloromethylketone (PPack), enoxaparin, angiopeptin, hirudin, angiopeptin, or monoclonal antibodies capable of blocking smooth muscle cell proliferation, acetylsalicylic acid, sirolimus its analogs and derivatives, tacrolimus, everolimus, amlodipine and doxazosin, glucocorticoids, betamethasone, dexamethasone, prednisolone, corticosterone, budesonide, amlodipine, doxazosin, estrogen, sulfasalazine, rosiglitazone, mycophenolic acid and mesalamine, paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives; cladribine, lidocaine, bupivacaine, ropivacaine, D-Phe-Pro-Arg chloromethyl ketone, platelet receptor antagonists, anti-thrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonist, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobramycin, angiogenic substances, fibroblast growth factors, estrogen, estradiol (E2), estriol (E3), 17-beta estradiol, digoxin, beta blockers, captopril, enalapril, statins, steroids, vitamins, 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl)glutamide hydrochloride salt, nitroglycerine, nitrous oxides, nitric oxides, antibiotics, aspirins, digitalis, estrogen, estradiol and glycosides, alofuginone; inhibitors of HSP90 heat shock proteins such as geldanamycin; microtubule stabilizing agents such as epothilone D; phosphodiesterase inhibitors such as cliostazole; bARKct inhibitors; phospholamban inhibitors; and Serca 2 gene/proteins The term "genetic materials" means DNA or RNA, including, without limitation, of DNA/RNA encoding a useful protein, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

The dosage or concentration of the therapeutic agent required to inhibit the desired cellular activity of the vascular region can depend upon factors such as the particular circumstances of the patient; the nature of the trauma, the nature of the therapy desired, the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

In a further embodiment, the medical device may also carry therapeutic agents, such as, for example, anti-spasmodic, anti-thrombogenic, and anti-platelet agents, antibiotics, steroids, and the like, in conjunction with the anti-proliferative agent, to provide local administration of additional medication.

The therapeutic agents may be formulated in normal way or may be encapsulated in the agents like oils, long chain fatty acids (as such or hydrogenated partially or fully), lipids (as such or hydrogenated partially or fully) or liposomes etc using sonication technique.

The method of coating the stent with therapeutic agents that may or may not be lipid encapsulated is designed so as to have proper distribution of coating onto the pores and on the plain surface to ensure desired pharmacokinetics and target delivery into the tissue. The proportions inside the pores and on the surface can be varied to suit the pore structure as well as pharmacokinetics.

Thus, a preferred embodiment comprises of a therapeutic formulation comprising of therapeutic agent/s mixed/bound with affinity vehicle/s together with suitable additives and solvent, which is capable of being coated on the surface (porous or non-porous) of implantable medical devices to deliver the desired concentration of therapeutic agent/s to the target site at doses of therapeutic agents lower than those in vogue and retaining the therapeutic agent for desired period of time. The formulation solution may contain 50%-95% solvent w/w, preferably 70%-95%. The coating on the stent may contain 20%-50% lipids (preferably 30%-45%), 50%-75% therapeutic agents and 0.1%-10% additives The affinity vehicle may include suitable lipid or modified lipid or a mixture thereof for the purpose of the present invention and may include phospholipids, mono, di and triglycerides of long chain fatty acids or any oil which is suitable for the purpose such as fats, waxes, cholesterol, sterols, fat-soluble vitamins (such as vitamins A, D, E and K), and others. This may also include a lipid or a mixture of lipids which are triglycerides of long chain fatty acids like vegetable oils (which may include Soya, Safflower, Castor, Sunflower oils or similar other oils) with varying amounts of free fatty acid and triglycerides. The affinity vehicles described above may be of natural or synthetic origin. The natural compounds may optionally be hydrogenated by well known methods to get partially or fully hydrogenated products with melting point higher than the original non-hydrogenated compounds. However, hydrogenation is not absolutely essential.

Additives may be a low molecular weight alkylated aromatic compound or a mixture of such compounds which may include but not limited to tertiary butyl phenols, tertiary butyl catechols, tertiary butyl cresols etc. or Tocopherols and their esters including all its isomers or combinations thereof.

A low molecular weight alcohol (C1 to C6) or a mixture of such alcohols or chlorinated hydrocarbons may be used as solvent to from homogeneous solution of all the components. In case the components are not soluble (fully or partially) in the solvent, they are emulsified using biocompatible emulsifiers or used as homogeneous slurry which can result into uniform coating on the device.

The following examples, which include preferred embodiments, will serve to illustrate the practice of this invention, it being understood that the particulars shown are by way of example and for purpose of illustrative discussion of preferred embodiments of the invention.

The example described below demonstrates the bioavailability of the formulation of therapeutic agent's coated on plain surface of the medical device like a coronary stent. The improved bioavailability of the invention is demonstrated by comparison between coronary stents coated with conventional formulations containing higher dose of therapeutic agent in polymers as vehicles and stents coated with invented formulation.

Though the example is for coronary stent with rapamycin as therapeutic agent, the invented formulation and imparting porosity to the surface are equally applicable to all medical devices and all other therapeutic agents as described supra. Similarly, the other components are not limited to lipids as described in the given example. The method is applicable to other components described in this patent application.

For clarity, the 'formulation' refers to the invented formulation and 'conventional formulation' refers to the formulation of therapeutic agent in polymers as vehicle. Similarly, the 'stent' refers to the stent coated with invented formulation and 'conventional stent' refers to the stent coated with formulation of therapeutic agent in polymers as vehicle. The conventional stents used for comparison are with plain surface.

The method of coating the stents with the formulation is also described below. This method gives uniform thin coating of the formulation over the entire surface of the stent.

Example 1

The formulation: The preferred formulation includes, but is not limited to, the following components.
1. The therapeutic agent/s.
2. A lipid or a mixture of lipids which are triglycerides of long chain fatty acids like vegetable oils (which may include Soya, Safflower, Castor, Sunflower oils or similar other oils) with varying amounts of free fatty acid and triglycerides.
3. A low molecular weight alkylated aromatic compound or a mixture of such compounds (referred to as "additive/s" hereinafter).
4. A low molecular weight alcohol or a mixture of such alcohols or chlorinated hydrocarbons used as solvents to from homogeneous solution of all the components.

The lipid/s and the additive/s can be chosen from a host of chemical compounds keeping in mind their (a) biocompatibility (b) physical affinity to the therapeutic agent/s and with each other (c) chemical compatibility to the therapeutic agent/s and with each other to prevent unwanted side reactions (d) hydrophilicity and hydrophobicity of the overall formulation and (e) the physical and chemical affinity of the formulation to the surface of the medical device which may be plain or porous. The solvent can be chosen from a number of candidates keeping in mind its solvent properties, biocompatibility and volatility.

The formulation may be sonicated before or during coating operation to facilitate encapsulation of the therapeutic agent/s into the lipid moiety if so desired.

The formulation should have desired adhesion to the surface of the medical device when coated and after evaporation of the solvent. Adhesion should be sufficiently strong to withstand physical forces during mounting the stent onto the balloon catheter and also prevent the formulation release during implantation of the stent. At the same time, the coating should have desired release properties after the implantation of the medical device. The components should have no undesired interactions with each other when they are being processed and also during the shelf life of the medical device.

Typical formulations are described below.
Typical Formulation No. 1
In one embodiment, the formulation had Sirolimus to oil (hydrogenated castor oil) ratio between 0.5-0.7 (w/w) and the formulation contained 0.25-0.4% (w/w) additive.

Typical Formulation No. 2
In another embodiment, the formulation had Sirolimus to oil (hydrogenated castor oil) ratio between 0.9-1.1 (w/w) and the formulation contained 0.35-0.5% (w/w) additive.

Typical Formulation No. 3
In still another embodiment, the formulation had Sirolimus to oil (castor oil) ratio between 1.2-1.4 (w/w) and the formulation contained 0.45-0.7% (w/w) additive.

Typical Formulation No. 4
In one embodiment, the formulation had Sirolimus to oil (castor oil) ratio between 1.8-2.0 (w/w) and the formulation contained 0.7-0.9% (w/w) additive.

The viscosity of these formulations when made in ethanol or dichloromethane as solvent varies from 0.3 to 0.8 centipoise.

Example 2

This example illustrates the effect of composition of the formulation on release profile of the therapeutic agent. This example describes specific therapeutic agent and specific vehicle for illustration only. This concept can be extended to other therapeutic agents and vehicles described supra.

Formulations with different ratios of therapeutic agent to vehicle were coated on the medical devices such as coronary stents. In these formulations, the therapeutic agent was Sirolimus and hydrogenated castor oil was the vehicle. These formulations were typically coated on coronary stents using validated coating technique. The release profile was checked in-vitro using proprietary release medium.

| Formulation No. | Proportion of Drug to vehicle |
| --- | --- |
| A | 50:50 |
| B | 60:40 |
| C | 70:30 |

Results of in-vitro Sirolimus release profile were as under (±10%).

| | % release of Sirolimus from the stent for above formulations | | |
| --- | --- | --- | --- |
| Time Hours | A | B | C |
| 0.5 | 45-46 | 54-55 | 60-61 |
| 1.0 | 55-56 | 63-64 | 70-71 |
| 3.0 | 68-69 | 73-74 | 78-79 |
| 6.0 | 75-76 | 79-80 | 84-85 |
| 24.0 | 85-86 | 89-90 | 92-93 |
| 48.0 | 90-91 | 94-95 | 97-98 |

As is evident from above results, the composition of the formulation has marked effect on the release profile of therapeutic agent.

Example 3

The coating process: To achieve good coating efficiency, high accuracy, overall control over the amount, uniform thickness of coating and uniform distribution of the therapeutic agent over the entire surface of the medical device, the spray-coating process is required to be controlled by an efficient programming of the entire process. Any coating machine that can meet these requirements can be used for coating process. In this example, the formulation coating process is performed using a micromist medicoat spray coating machine obtained from SONO-TEK Corporation, USA. The Spray coating machine is provided with one micro mist nozzle (located in vertical direction) which carries an inert gas like nitrogen (used as carrier) and two side nozzles (located in horizontal direction). The former is for spraying formulation and the latter are for wetting with the solvent/s to remove the excess therapeutic agent/s and lipid from the medical device to ensure uniformity in coating. The process sequence typically consists of first purging of inert gas to remove the foreign particles, if any. This is followed by repeat cycles of spraying the formulation followed by wetting. The number of cycles depends on specific coating requirements. This sequence can be well validated to achieve desired results and it can be controlled by automated operation program. The invented coating method is efficient and can be validated to achieve very uniform thin coating on a medical device even if it has complicated surfaces. The coating formulation, comprising of therapeutic agent/s, lipid/s, additive/s and solvent/s, can be applied to the surface of a medical device using a single feed ultrasonic nozzle. This machine has a medicoat bench top glove box type enclosure. The formulation and wetting solution syringes are fitted to pumps located on one side of the coating chamber. The formulation is placed into the syringe and the syringe is fitted to the pump. Electrostatically charged finely divided droplets of coating formulation are created through the nozzle and deposited onto the grounded surface of the medical device to form a coating on its surface. The coating produced by the method of present invention is completely uniform. In particular, when a coating formulation is applied to a stent having a tubular sidewall and openings therein, the coating on both the inside and outside surfaces of the stent's sidewall is uniform.

There is another advantage of the coating method of the present invention. Because the atomization in the gas is conducted solely using electrostatic forces, each droplet has very little tendency to deviate from the path to which it is directed. Accordingly, a spray mist containing such droplets is less likely to miss the target surface. This provides a much more efficient means for applying a coating formulation to the surface of a medical device. More specifically, a major portion of the coating formulation that is sprayed gets deposited on the surface giving high coating accuracy and at the same time minimizing the losses and environmental contamination.

Several operating parameters can be manipulated to get optimum coating properties. These parameters are (i) inert gas pressure (ii) ultrasonic power (iii) rotational speed of the medical device (such as a stent) (iv) flow rate of the formulation (v) flow rate of the solvent and (vi) distance of spray nozzle from the outer surface of the device being coated. Manipulation of all these parameters gives excellent flexibility to optimize quality of the coating. In typical embodiments for coating coronary stents, following parameters were used typically.

1. Inert gas pressure: 0.5-7.5 psig.
2. Ultrasonic power: 0.8-1.8 watts
3. Rotational speed of the stent: 80-150 RPM
4. Flow rate of formulation: 8-25 microliters/min
5. Flow rate of solvent: 30-80 microliters/min
6. Distance of spray nozzle from device surface: 5-15 mm The coated medical devices are kept in the vacuum oven at required reduced pressure for minimum 12 hrs to maximum 24 hrs at appropriate temperature for vacuum drying. This operation removes the solvent/s from the coating. The coating machine and the coating process can be made suitable and well validated for the specific formulation and specific surface of the device.

Example 4

Comparison with Conventional Stents and the Study Method

The stents coated with invented formulation were implanted in left and right iliac arteries of rabbits and tissue was examined after the intervals of 1, 3, 14 and 28 days. Drug elution and blood samples at various time points were also examined. Conventional stent-1 were also implanted along with these stents as control for comparison.

The comparison was made with two types of conventional stents as under.

Conventional Stent-1

The same bare metal stents (with plain surface) were coated with rapamycin formulated in biodegradable polymers. The drug dose was 0.7 micrograms per $mm^2$ of the stent area. The total loading of rapamycin on the stent of 3 mm dia, 13 mm length was 40 micrograms. The formulation had 36-37% rapamycin and 63-64% bio degradable polymers Poly(L-lactide) and Poly(DL-lactide-co-glycolide) in the ratio 3.5:1. These stents were implanted in rabbits as control samples along with stents coated with invented formulation.

Conventional Stent-2

Comparison was also made with conventional stent coated with conventional formulation of rapamycin in polymers as vehicle for which the data was obtained from literature. The dose of rapamycin in these stents was 1.4 micrograms per $mm^2$ of stent surface area. For the stent surface area same as Conventional stent-1, the drug dose would amount to 80 micrograms. Though the available literature data was for porcine model, the comparison of results obtained on rabbit iliac gives a clear conclusion on superiority of the invented formulation.

Inventive Stent with Formulation 3:

This example demonstrates the superior bioavailability of the invented formulation coated on porous surface of coronary stent compared to conventional stents coated with conventional formulations using same therapeutic agent but polymer/s as vehicle for controlled release.

The formulation was made using a lipid, rapamycin as therapeutic agent and a low molecular weight alkyl cresol with alkyl chain containing 3 to 6 carbon atoms as additive; all dissolved in ethyl alcohol as solvent. The formulation was coated on the surface of a coronary stent 3 mm dia and 13 mm long made from cobalt chromium alloy using sonication techniques as described above. The coating process as described above was used to achieve uniform thin coating of the formulation with rapamycin dose of 0.56 micrograms per $mm^2$ of the stent surface. The stent surface was with pores. The total loading of rapamycin on the stent was 31.5 micrograms.

The stents were implanted in left and right iliac arteries of rabbits and tissue was examined after the intervals of 1, 3, 14 and 28 days. Blood samples and drug elution at various time points were also examined. Following results were obtained.

1. For the stent, more than 80% of the drug was released at day 1 and 97% at day 7. The stent did not show any coating at the end of 7 days showing exposed metal.

In comparison, the Conventional stent-1 showed release of 25% of the drug at day 1 and 77% at day 7. It reached 88% at day 14 and 95% at day 28.

The Conventional stent-2 reported release of ~18% of the drug at day 1 and 45% at day 7. It reached 80% at day 28 and 95% at day 90.

This comparison shows that the release of invented formulation is much faster than from conventional stents.

2. For the stent, the concentration of rapamycin in blood stream of the animal (rabbit) was very low throughout the trial. This concentration dropped substantially after 24 hrs of implantation (0.56 ng/ml).

In comparison, for the Conventional stent-1, rapamycin concentration in the blood of the animal (rabbit) reached 3.1 ng/ml in 24 hours of implantation.

For Conventional stent-2, the rapamycin concentration in the blood of the animal (swine) reaches 0.4 ng/ml in 24 hours of implantation. This comparison is not very accurate because this data for Conventional stent-2 is reported for swine model.

3. The artery homogenate showed substantially high concentration of drug for the stent compared to conventional stent. On day 1, for the Stent, the drug concentration was ~210 ng/mg of artery homogenate. This concentration reduced to 180, 50, 40 and 26 ng/mg on day 3, 7, 14 and 28 respectively. It is evident that even on day 28, the drug concentration in artery homogenate is considerably high.

In comparison, the Conventional stent-1 showed tissue concentration of 12 ng/mg of artery homogenate on day 1. This concentration reduced to 1.2, 1.5, 6.8 and 0.7 ng/mg on day 3, 7, 14 and 28 respectively.

The Conventional stent-2 reports tissue concentration of 10 ng/mg of artery homogenate on day 1. This concentration reduced to 8, 4, 8 and 2 ng/mg on day 3, 7, 14 and 28 respectively.

Inventive Stent with Formulation 4:

This example demonstrates the superior bioavailability of the invented formulation coated on plain surface of coronary stent compared to conventional stents coated with conventional formulations using same therapeutic agent but polymer/s as vehicle for controlled release.

The formulation was made using a lipid, rapamycin as therapeutic agent and a low molecular weight alkyl cresol with alkyl chain containing 3 to 6 carbon atoms as additive; all dissolved in ethyl alcohol as solvent. The formulation was coated on the surface of a coronary stent 3 mm dia and 13 mm long made from cobalt chromium alloy using sonication techniques as described above. The coating process as described above was used to achieve uniform thin coating of the formulation with rapamycin dose of 0.3 micrograms per $mm^2$ of the stent surface. The stent surface was plain and did not have pores. The total loading of rapamycin on the stent was 16.9 micrograms.

The stents were implanted in left and right iliac arteries of rabbits and tissue was examined after the intervals of 8 and 28 days. Following results were obtained.

For the stent, more than 90% of the drug was released at day 8 and more than 98% at day 28. The stent did not show any coating at the end of 8 days showing exposed metal.

The artery homogenate showed substantially high concentration of drug for the stent compared to conventional stent. On day 1, for the Stent, the drug concentration was ~107 ng/mg. This concentration reduced to 8 ng/mg on day 28. It is evident that even on day 28, the drug concentration in artery homogenate is considerably higher compared to that for conventional stents described in Example 3 above.

This shows that the tissue concentration for the stent coated with invented formulation is substantially higher over the conventional models.

Thus, the invented formulation and coating method result in target drug delivery with very little loss to the blood stream. In addition, the drug availability is nearly total. The dose of rapamycin (0.56 micrograms/$mm^2$ and 0.3 micrograms/$mm^2$) is much lower than conventional doses of 0.7 and 1.4 micrograms/$mm^2$. Even at such high doses, drug concentrations in artery homogenate are much lower for conventional formulations compared to those achieved in case of invented stents.

The therapeutic formulation according to the present invention is capable of being removed completely from the surface of the implantable medical device over desired time.

Comparison Table Results of In Vivo Test on Animals

| Parameters | Conventional Stent-1 | Conventional Stent-2 | Inventive Stent-1 (porous surface) | Inventive Stent-2 (plain surface) |
|---|---|---|---|---|
| Sirolimus dose micrograms/$mm^2$ | 0.7 | 1.4 | 0.56 | 0.3 |
| Total drug content on 3 × 13 stent | 40 micrograms | 80 micrograms | 31.5 micrograms | 16.9 micrograms |
| Vehicle used | Biodegradable polymers | Non-biodegradable polymers | Lipid | Lipid |
| Animal model | Rabbit | Porcine | Rabbit | Rabbit |
| Drug released | | | | |
| Day-1 | 25% | 18% | >80% | |
| Day-7/8 | 77% | 45% | 97% | >90% |
| Day-14 | 88% | | | |
| Day-28 | 95% | 80% | | >98% |
| Day-90 | | 95% | | |
| Drug in blood ng/ml, 24 hrs | 3.1 (Rabbit) | 0.4 (Porcine) | 0.56 (Rabbit) | |
| Drug in tissue ng/mg | | | | |
| Day-1 | 12 | 10 | 210 | 107 |
| Day-3 | 1.2 | 8 | 180 | |
| Day-7 | 1.5 | 4 | 50 | |

-continued

| Parameters | Conventional Stent-1 | Conventional Stent-2 | Inventive Stent-1 (porous surface) | Inventive Stent-2 (plain surface) |
|---|---|---|---|---|
| Day-14 | 6.8 | 8 | 40 | |
| Day-28 | 0.7 | 2 | 26 | 8 |

The implantable medical device according to the present invention, the said affinity vehicle allows the therapeutic agent to be retained into the tissue of the vessel wall for desired period of time and to diffuse in a controlled manner into the tissue of the vessel wall.

It is to be understood that the embodiments and variations shown and described herein are merely illustrative of the principles of the present invention. Therefore, various adaptations and modifications may be implemented by those skilled in the art without departing from the spirit and scope of the present invention.

The invention claimed is:

1. A formulation for targeted delivery of lipophilic therapeutic agent, comprising:
   (a) at least one lipophilic therapeutic agent in the range of 50%-70% by weight of formulation,
   (b) at least one non polymeric bio-absorbable affinity vehicle or carrier selected from the group consisting of low melting vegetable oils containing triglycerides of long chain fatty acids with varying amounts of free fatty acids in the range of 30%-50% by weight of the formulation, and
   (c) an additive in the range of 0.2% to 0.4% by weight of the formulation, said additive being selected from the group consisting of alkylated aromatic compounds having anti-oxidant properties with molecular weights in the range of 100-500 or a mixture of such compounds,
   wherein the formulation is devoid of any polymer,
   wherein the melting point of the affinity vehicle or the carrier is between −10 and −18 degree Celsius, and
   wherein the affinity vehicle or carrier compound comprises castor oil.

2. A formulation of claim 1, wherein the therapeutic agent is selected from the group consisting of antiproliferative agents, anti-inflammatory agents, antithrombotic agents, urokinase, hirudin; sirolimus, everolimus, tacrolimus, zotarolimus and their analogs and derivatives.

3. A formulation of claim 1, wherein the additive is selected from the group consisting of tertiary butyl phenols, tertiary butyl catechols, tertiary butyl cresols, tocopherols, isomers thereof, esters thereof, and mixtures thereof.

4. A medical device having a plain surface, wherein the formulation of claim 1 is coated on the plain surface of the medical device, wherein at least 90% of the dose of the therapeutic agent is delivered to the targeted tissue of the mammal within maximum 28 days from the implantation.

5. A medical device having a plain surface, wherein the formulation of claim 1 is coated on the plain surface of the medical device, wherein more than 98% of the dose of the therapeutic agent is delivered to the targeted tissue of the mammal within maximum 28 days from the implantation.

6. A medical device having a porous surface, wherein the formulation of claim 1 is coated on the porous surface of the medical device, the medical device having cavities ranging from about 1 nm to 1.5 µm in size and 10 nm to 3 µm in depth; wherein the said cavities on the porous surface have uniform and/or random pore structure; wherein cavities on the porous surface have oriented or directional grain pore structure, wherein at least 90% of the dose of the therapeutic agent is delivered to the targeted tissue of the mammal within maximum 28 days from the implantation.

7. A medical device having a porous surface, wherein the formulation of claim 1 is coated on the porous surface of the medical device, the medical device having cavities ranging from about 1 nm to 1.5 µm in size and 10 nm to 3 µm in depth; wherein said cavities on the porous surface have uniform and/or random pore structure; wherein the cavities on the porous surface have oriented or directional grain pore structure, wherein more than 98% of the dose of the therapeutic agent is delivered to the targeted tissue of the mammal within maximum 28 days from the implantation.

8. A medical device having a surface, wherein the formulation of claim 1 is coated on the surface of the medical device, wherein the therapeutic agent is Sirolimus in an amount of 0.56 micrograms/mm$^2$, wherein after implantation of the medical device at a target site of a subject, the tissue concentration of the therapeutic agent at the target site is more than 200 nanograms/mg to around 50 nanograms/mg between Day −1 and Day −7 and in the range of 40 nanograms/mg to 26 nanograms/mg between Day −14 and Day −28.

9. A medical device having a surface, wherein the formulation of claim 1 is coated on the surface of the medical device, wherein the therapeutic agent is Sirolimus in an amount of 0.3 micrograms/mm$^2$, wherein after implantation of the medical device at a target site of a subject, the tissue concentration of the therapeutic agent at the target site is more than 100 nanograms/mg on Day-1, and about 8 nanograms/mg on Day-28.

10. A medical device coated with the formulation of claim 1 wherein the surface of such device is plain; and wherein the thickness of the coating is 1 micron or less, wherein at least 90% of the dose of the therapeutic agent is delivered to the targeted tissue of the mammal within maximum 28 days from the implantation.

11. A medical device coated with the formulation of claim 1 wherein the surface of the device is porous having cavities ranging from about 1 nm to 1.5 µm in size and 10 nm to 3 µm in depth; wherein the said cavities on the porous surface have uniform and/or random pore structure; wherein the cavities on the porous surface have oriented or directional grain pore structure; and wherein the thickness of the coating is 1µ (micron) or less, wherein more than 90% of the dose of the therapeutic agent is delivered to the targeted tissue of the mammal within maximum 28 days from the implantation.

12. A medical device coated with the formulation of claim 1 wherein the surface of such device is plain; and wherein the thickness of the coating is 1µ (micron) or less, wherein at least 98% of the dose of the therapeutic agent is delivered to the targeted tissue of the mammal within maximum 28 days from the implantation.

13. A medical device coated with the formulation of claim 1 wherein the surface of the device is porous having cavities ranging from about 1 nm to 1.5 µm in size and 10 nm to 3 µm in depth; wherein the said cavities on the porous surface have uniform and/or random pore structure; wherein the cavities on the porous surface have oriented or directional grain pore structure; and wherein the thickness of the coating is 1μ (micron) or less, wherein more than 98% of the dose of the therapeutic agent is delivered to the targeted tissue of the mammal within maximum 28 days from the implantation.

14. A medical device coated with the formulation of claim 1, wherein the medical device is a stent.

* * * * *